United States Patent
Tomiyama et al.

(10) Patent No.: US 7,439,402 B2
(45) Date of Patent: Oct. 21, 2008

(54) METHOD FOR PRODUCING QUINONE COMPOUND

(75) Inventors: Tadashi Tomiyama, Kamisu (JP); Akisuke Saika, Kitamoto (JP)

(73) Assignee: Eisai R&D Management Co., Ltd., Bunkyo-ku, Tokyo (JP)

( * ) Notice: Subject to any disclaimer, the term of this patent is extended or adjusted under 35 U.S.C. 154(b) by 34 days.

(21) Appl. No.: 11/520,734

(22) Filed: Sep. 14, 2006

(65) Prior Publication Data

US 2007/0060761 A1    Mar. 15, 2007

Related U.S. Application Data

(60) Provisional application No. 60/716,950, filed on Sep. 15, 2005.

(51) Int. Cl.
C07C 45/29   (2006.01)
C07C 50/12   (2006.01)
C07C 50/14   (2006.01)

(52) U.S. Cl. .......................... 568/347; 552/296; 552/299

(58) Field of Classification Search ........................ None
See application file for complete search history.

(56) References Cited

U.S. PATENT DOCUMENTS

| | | | | |
|---|---|---|---|---|
| 4,199,531 | A | * | 4/1980 | Terao et al. .................... 568/33 |
| 5,220,042 | A | * | 6/1993 | Iwaki et al. ................... 552/307 |
| 5,637,716 | A | * | 6/1997 | Komatsu et al. ............. 546/301 |
| 2005/0137380 | A1 | * | 6/2005 | Mahalingam et al. ....... 528/196 |

FOREIGN PATENT DOCUMENTS

| | | |
|---|---|---|
| JP | 39-17514 | 8/1964 |
| JP | 48-49733 | 7/1973 |
| JP | 49-36642 | 4/1974 |
| JP | 49-55650 | 5/1974 |
| JP | 52-072884 | 6/1977 |
| JP | 54-5958 | 1/1979 |
| JP | 54-151932 | 11/1979 |
| JP | 62-081347 | 4/1987 |

OTHER PUBLICATIONS

Kozlov, E. I., Meditsinskaya Promyshlennost SSSR (1965), 19(4), 16-21.

* cited by examiner

*Primary Examiner*—Sikarl A Witherspoon
(74) *Attorney, Agent, or Firm*—Birch, Stewart, Kolasch & Birch, LLP

(57) ABSTRACT

A method for producing menatetrenone that does not have a deleterious influence on the environment, that is safe even when applied to large-scale production, and that is also simple to operate, wherein a compound represented by the following formula (1)

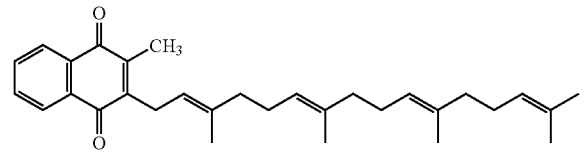

(1)

is produced by treating with an oxygen source, and without the addition of an additive other than water or aqueous sodium chloride solution, a reaction solution consisting essentially of a solution of a compound represented by the following formula (2) dissolved in a solvent:

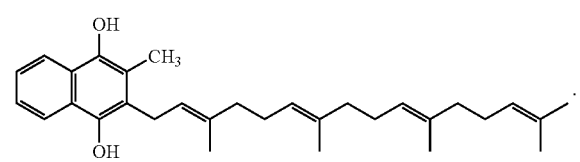

(2)

3 Claims, No Drawings

METHOD FOR PRODUCING QUINONE COMPOUND

CROSS-REFERENCES TO RELATED APPLICATIONS

The present application claims priority from U.S. Provisional Application No. 60/716,950 filed on Sep. 15, 2005.

BACKGROUND OF THE INVENTION

1. Field of the Invention

The present invention relates to a method for producing menatetrenone, which is a quinone compound.

2. Description of the Related Art

Menatetrenone is a compound represented by the following formula (1),

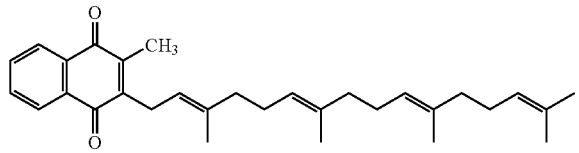

(1)

and vitamin $K_2$ formulations, which contain this compound as an active ingredient, are used for the prevention and treatment of vitamin K deficiency diseases and are also used as preventive and therapeutic agents for osteoporosis.

Menatetrenone is also present in, for example, fermented soybeans (natto), which is a fermented food, but the industrial methods of menatetrenone production are mainly based on chemical synthesis.

It is known that there are several methods for producing menatetrenone by chemical synthesis. As one example of several methods, it is known that a hydroquinone precursor is oxidized to give menatetrenone, the target quinone (Kozlov, E. I., *Meditsinskaya Promyshlennost* SSSR (1965), 19(4), 16-21).

The method disclosed in Kozlov uses silver oxide, it is known that there are methods that similarly use metal oxides such as manganese dioxide, lead peroxide (Japanese Patent Application Laid-open No. 49-55650), and so forth.

However, there were drawbacks to the use of metal oxides; for example, the reaction was difficult to control and there was a risk that side reactions would occur. Moreover, the use of metal oxides made it necessary to carry out a post-reaction treatment in order to prevent adverse effects on the environment.

In view the above, it has been developed that a method uses hydrogen peroxide (Japanese Patent Application Laid-open No. 48-49733).

Hydrogen peroxide is, however, a powerful oxidizing agent, and the handling of hydrogen peroxide in large amounts requires special handling with a particular emphasis on safety.

On the other hand, with regard to the production of ubiquinones, which are structurally similar to menatetrenone, it is known that methods use molecular oxygen, which is a milder oxidizing agent (Japanese Patent Publication No. 39-17514 and Japanese Patent Application Laid-open Nos. 52-72884, 54-151932, and 62-81347).

However, it was recognized that when using molecular oxygen in the method for the production of ubiquinones, the reaction rate with oxygen alone was very low and complete oxidation was not to be expected (Japanese Patent Application Laid-open Nos. 54-151932 and 62-81347). In order to overcome this problem, it is known that it is essential to add a base (Japanese Patent Application Laid-open No. 52-72884), silica gel (Japanese Patent Application Laid-open No. 54-151932), or copper or copper ion and ammonia or ammonium ion (Japanese Patent Application Laid-open No. 62-81347) to the reaction solution. These methods that use an additive in addition to the oxidizing agent have the problems encountered for the aforementioned use of the metal oxide to produce quinone, i.e., a risk of side reactions in the presence of the additive and complexity in post-reaction treatment.

In addition, as methods for producing menatetrenone, a specific method that uses molecular oxygen has heretofore been entirely unknown.

SUMMARY OF THE INVENTION

An object of the present invention, therefore, is to provide a method for producing menatetrenone that does not have a deleterious influence on the environment, that is safe even when applied to large-scale production, and that is also simple to operate.

As mentioned above, there were problems with the prior art methods for producing menatetrenone. The present inventors carried out focused investigations into methods for oxidizing the hydroquinone (2), which is a precursor for menatetrenone, and as a result, surprisingly discovered that, using molecular oxygen, a satisfactory reaction rate can be obtained and the oxidation reaction will run to completion, entirely without the use of additives and without the occurrence of significant side reactions. This was completely unforeseen given that it was a long-running matter of common knowledge in the art that the use of molecular oxygen alone as the oxidizing agent would give a very low reaction rate and could not be expected to give complete oxidation.

Moreover, it was additionally discovered that, by also having water be present in the reaction solution, the safety could be improved, although this has no influence on the oxidation reaction itself. Based on this finding, it was discovered that menatetrenone can be produced by a method that does not have a deleterious influence on the environment, that is safe even when applied to large-scale production, and that is also simple to operate, thereby reaching at the present invention.

That is, in a first aspect, the present invention provides a method for producing a compound represented by the following formula (1):

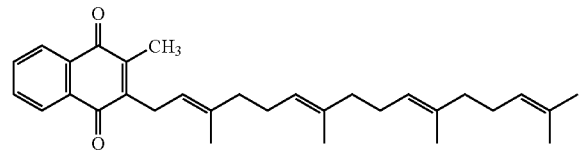

(1)

wherein a reaction solution consisting essentially of a solution of a compound represented by the following formula (2) dissolved in a solvent is treated with an oxygen source.

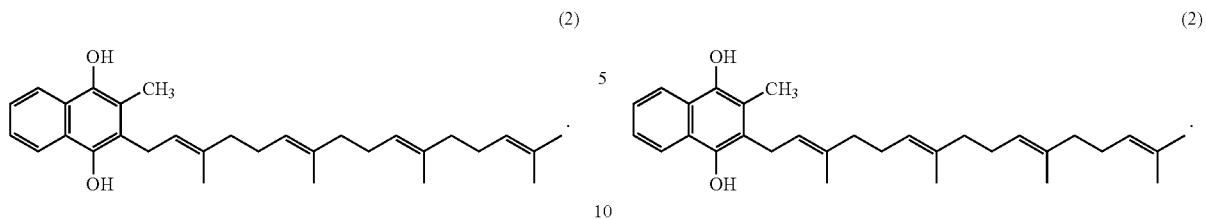
(2)

In a second embodiment aspect, the present invention provides a method for producing a compound represented by the following formula (1),

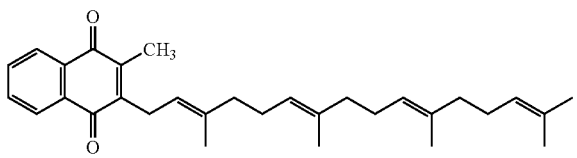
(1)

wherein a reaction solution consisting essentially of
i) a solution of a compound represented by the following formula (2) dissolved in a water-immiscible organic solvent and
ii) water or aqueous sodium chloride solution is treated with an oxygen source.

The oxygen source in the first and second aspects is preferably air, and treatment with the oxygen source is preferably carried out by blowing the oxygen source into the reaction solution.

The present invention enables the production of menatetrenone by a method that does not have a deleterious influence on the environment, that is safe even when applied to large-scale production, and that is also simple to operate.

DETAILED DESCRIPTION OF THE INVENTION

Hydroquinone (2) used in the present invention as a precursor for menatetrenone is a known substance and several methods are known for its synthesis. For example, it can be synthesized by the following route, which is disclosed in Kozlov.

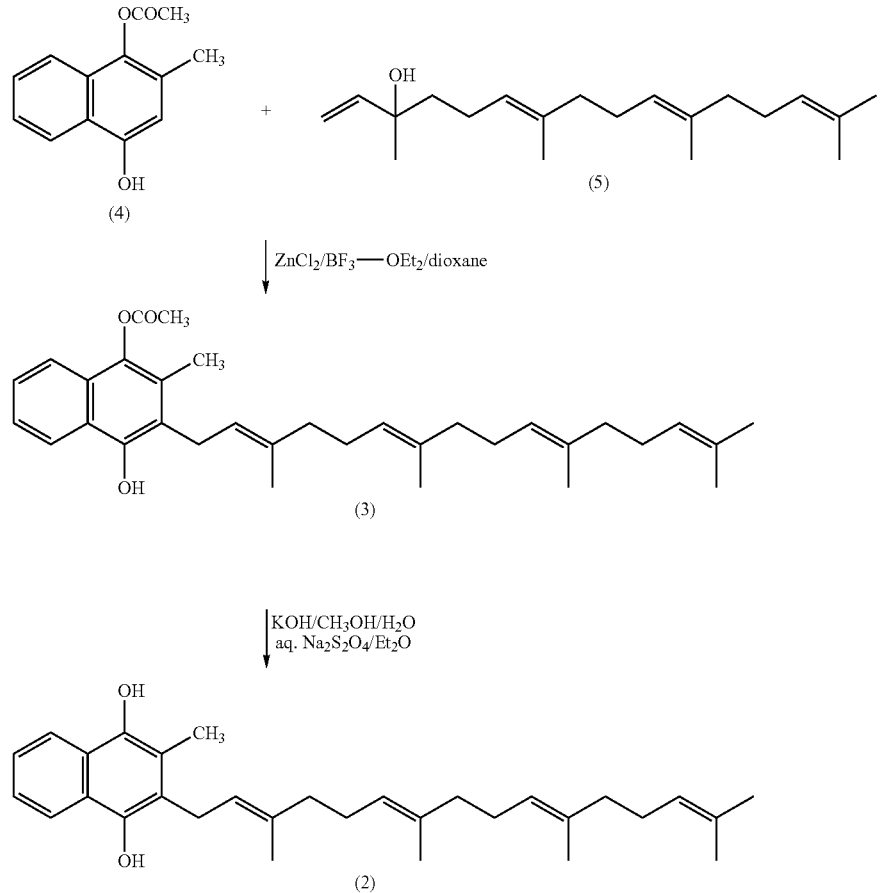

As set out above, the hydroquinone (2) can be synthesized by condensing menadiol monoacetate (4) and all-trans-geranyllinalool (5), followed by treatment with Claisen's alkaline solution.

The condensation reaction between menadiol monoacetate (4) and all-trans-geranyllinalool (5) can be carried out, as disclosed in Koziov, by heating menadiol monoacetate (4), zinc chloride, and boron trifluoride in dioxane to 50° C.; adding a dioxane solution of all-trans-geranyllinalool (5) to the reaction mixture dropwise over 30 minutes; and thereafter holding the reaction mixture at 50° C. for 30 minutes.

Besides dioxane, any solvent that does not inhibit the reaction can be employed as the solvent used in this condensation reaction. Examples of the solvent used in this condensation reaction include carbon tetrachloride, dichloromethane, chloroform, n-pentane, n-hexane, N,N-dimethylformamide, N-methylpyrrolidone, acetonitrile, dimethyl sulfoxide, benzene, toluene, xylene, methanol, ethanol, n-propanol, isopropanol, tert-butyl alcohol, methyl acetate, ethyl acetate and the like. Such solvent can be used singly, or in combination of two or more thereof in any proportion.

Acid catalysts other than the above zinc chloride and $BF_3$-$OEt_2$ can also be used. Examples of acid catalysts include oxalic acid; metal salts such as potassium sulfate, potassium persulfate, zinc(II) triflate, and copper(I) sulfate; and sulfonic acid derivatives such as p-toluenesulfonic acid, methanesulfonic acid, sulfophthalic acid, hydroxybenzenesulfonic acid, nitrobenzenesulfonic acid, benzenesulfonic acid, chlorobenzenesulfonic acid, naphthylsulfonic acid, dodecylbenzenesulfonic acid, 4,4'-biphenyldisulfonic acid and flavianic acid.

As disclosed in Kozlov, Claisen's alkaline (prepared by the dissolution of 35 g KOH in 25 mL water followed by dilution to 100 mL with $CH_3OH$) is added to the monoacetyl form (3) obtained by the condensation reaction; 3% aqueous hydrosulfite solution and ether are added thereto; the mixture is stirred; and the layers are then separated to obtain the hydroquinone (2) as the ether solution. Extraction solvents other than ether can be used after the Claisen treatment, and examples of extraction solvents include carbon tetrachloride, dichloromethane, chloroform, n-pentane, n-hexane, N-methylpyrrolidone, benzene, toluene, xylene, tert-butyl alcohol, methyl acetate, ethyl acetate and the like. Such solvent can be used singly, or in combination of two or more thereof in any proportion.

The next step is the oxidation reaction of the production method according to the present invention. Hydroquinone (2) extract obtained in the preceding step may be directly used in the present invention, or the solvent may be changed by removing the extraction solvent by, for example, distillation under reduced pressure. In any event, it is simply sufficient to prepare a solution in which hydroquinone (2) is dissolved in a solvent, and, except for the addition of water or aqueous sodium chloride solution as described below, the addition of any other additive is unnecessary. There are no particular limitations on the solvent as long as the solvent can dissolve hydroquinone (2) and does not inhibit the oxidation reaction. Examples of the solvent include carbon tetrachloride, dichloromethane, chloroform, n-pentane, n-hexane, N,N-dimethylformamide, N-methylpyrrolidone, acetonitrile, dimethyl sulfoxide, benzene, toluene, xylene, methanol, ethanol, n-propanol, isopropanol, tert-butyl alcohol, methyl acetate, ethyl acetate and the like. Such solvent can be used singly, or in combination of two or more thereof in any proportion. A water-containing solvent can also be used.

The method according to the present invention can be carried out using only a solution in which hydroquinone (2) is dissolved in the solvent. That is, it is not necessary to add any other additive in order for the oxidation reaction to proceed to completion. However, based on safety considerations, it is preferable that the reaction used in the present invention be carried out in a two-layer system obtained by the addition of water or aqueous sodium chloride solution. In the case of the reaction in a two-layer system, it is preferable to use a water-immiscible organic solvent as the solvent. Examples of the water-immiscible organic solvent include carbon tetrachloride, dichloromethane, chloroform, n-pentane, n-hexane, N-methylpyrrolidone, benzene, toluene, xylene, tert-butyl alcohol, methyl acetate, ethyl acetate, or a mixed solvent of at least two of the foregoing. As to whether water or aqueous sodium chloride solution is to be used, the appropriate selection may be made based on the solvent used. For example, the one that provides the better separation between the organic and water layers during post-reaction layer separation can be selected.

The term "oxygen source" used in the present invention refers to an oxygen source that can introduce molecular oxygen into the reaction system, for example, oxygen gas or air. When oxygen gas or air is used as the oxygen source, it can be used in the form of a mixed gas with another gas that does not impair the present invention, for example, nitrogen, helium, or argon.

Effective contact between the reaction substrate in the reaction solution and the molecular oxygen that is introduced into the reaction system is preferably induced by blowing the oxygen source into the reaction solution. When, for example, air is blown into the reaction solution, it can be blown through a nozzle; it can be blown into the reaction solution into bubbles through a porous element provided at the end of a nozzle; it can be blown out from numeraous holes on a ring-shaped pipe provided in the reaction vessel into bubbles of an appropriate size; or various other mechanical means can be implemented.

The temperature conditions of the oxidation reaction according to the present invention can be suitably selected from the view points of efficiency of reaction, that is, the temperature conditions can vary depending on types of the solvent used, efficiencies of contact with the oxygen source and the like. The reaction can be carried out at from 0° C. up to the boiling point of the solvent, however, taking into account of such factors as the reaction time and the energy efficiency, the reaction temperature is preferably room temperature to 60° C., more preferably 20 to 50° C., most preferably 30 to 40° C. The reaction time can be selected as appropriate by monitoring the completion of the reaction by TLC or HPLC and is preferably from 3 hours to 20 hours; there is no reduction in yield due to side reactions even after reaction overnight for about 15 hours.

After completion of the oxidation reaction, menatetrenone is obtained by conventional work up and purification. Specifically, the reaction solution may be concentrated, for example, under reduced pressure, to obtain a crude product, which may then be purified by column chromatography and/or recrystallization. From the standpoint of safety, the reaction solution is preferably concentrated after it has been washed with water, and in this context again the solvent used in the oxidation reaction is preferably a water-immiscible organic solvent.

EXAMPLE

The present invention is explained in terms of specific examples by the examples provided hereinbelow, but the present invention is not limited to these examples.

Example 1

First Step (Condensation Reaction)

Menadiol monoacetate (4) (28.8 g) was dissolved in a mixed solvent of ethyl acetate (67 mL) and n-hexane (67 mL) and $BF_3$-$Et_2O$ (2.4 g) was added thereto. While stirring this solution, all-trans-geranyllinalool (5) (28.3 g) was added dropwise at 45° C. over about 1 hour and 30 minutes to 2 hours, the reaction was then carried out for 5 hours at the same temperature. The reaction solution was then washed four times with aqueous sodium chloride solution (20 mL, 5%). The organic layer was subsequently washed four times with a solution prepared by the addition of sodium hydrosulfite (2 g) to aqueous potassium hydroxide solution (40 mL, 10%). The organic layer was also washed an additional four times with aqueous sodium chloride solution (20 mL, 5%). The organic layer was concentrated under reduced pressure.

Second Step (Treatment with Claisen's Alkaline)

The concentrated residue was dissolved in toluene (150 mL), and sodium hydrosulfite (4 g), potassium hydroxide (23 g), water (17 mL), and methanol (40 mL) were added thereto and stirred. The toluene layer was removed by layer separation; the aqueous layer was washed with toluene (90 mL); ethyl acetate (100 mL), n-hexane (100 mL), and water (220 mL) were added to the aqueous layer and the aqueous layer was extracted; and the organic layer was washed twice with aqueous sodium chloride solution (20 mL, 5%) followed by layer separation.

Third Step Three (Oxidation Reaction)

Aqueous sodium chloride solution (prepared from 14 g NaCl and 80 mL water) and n-hexane (200 mL) were added to the organic layer and the reaction mixture was then stirred while bubbling air into it. The layers were separated after the completion of the reaction and the organic layer was washed three times with water (30 mL) and was concentrated. The concentrated residue was subjected to column chromatography (n-hexane) and the fraction containing the target material was concentrated, yielding crude menatetrenone as an oil. The crude menatetrenone was crystallized from ethanol to give crude crystals. Menatetrenone (1) was obtained (22% yield from (5)) by recrystallizing the crude crystals from ethanol.

Example 2

First Step (Condensation Reaction)

Menadiol monoacetate (4) (26 g) was dissolved in toluene (130 mL), and, while stirring at 50° C., a solution of all-trans-geranyllinalool (5) (29 g) dissolved in toluene (10 mL) and a solution of $BF_3$-$Et_2O$ (3.6 g) dissolved in toluene (20 mL) were both added dropwise at the same time over 30 minutes. The reaction was then carried out for 30 minutes at the same temperature. The reaction solution was washed with aqueous sodium chloride solution (40 mL, 5%) twice. The organic layer was washed twice with a solution prepared by the addition of sodium hydrosulfite (2 g) to aqueous potassium hydroxide solution (60 mL, 10%).

Second Step (Treatment with Claisen's Alkaline)

To the organic layer were added sodium hydrosulfite (3 g), potassium hydroxide (23 g), water (17 mL), and methanol (40 mL) and the reaction mixture was stirred. The toluene layer was removed by layer separation; the aqueous layer was washed with toluene (140 mL); toluene (200 mL), acetic acid (30 mL), and water (220 mL) were added to the aqueous layer and the aqueous layer was extracted. The organic layer was washed with aqueous sodium chloride solution (40 mL, 5%) twice, followed by layer separation.

Third Step (Oxidation Reaction)

Water (80 mL) was added to the organic layer and the mixture was stirred while blowing air into the mixture. After completion of the reaction, the layers were separated and the organic layer was washed with water (30 mL) three times and was then concentrated to give crude menatetrenone.

Example 3

First Step (Condensation Reaction)

Menadiol monoacetate (4) (30.5 g) and all-trans-geranyllinalool (5) (28.3 g) were dissolved in toluene (130 mL), and, while stirring at 45° C., a solution of $BF_3$-$Et_2O$ (2.1 g) dissolved in toluene (20 mL) was added dropwise over 30 minutes. The reaction was then continued for 60 minutes at the same temperature. The reaction solution was washed with aqueous sodium chloride solution (40 mL, 5%). The organic layer was washed twice with a solution prepared by addition of sodium hydrosulfite (2 g) to aqueous potassium hydroxide solution (60 mL, 10%).

Second Step (Treatment with Claisen's Alkaline)

To the organic layer were added sodium hydrosulfite (4 g), potassium hydroxide (23 g), water (17 mL), and methanol (40 mL) and the reaction mixture was stirred. The toluene layer was removed by layer separation; the aqueous layer was washed with toluene (100 mL); n-hexane (100 mL), ethyl acetate (100 mL), and water (220 mL) were added to the aqueous layer and the aqueous layer was extracted, and the organic layer was washed twice with aqueous sodium chloride solution (40 mL, 5%), followed by layer separation.

Third Step (Oxidation Reaction)

n-Hexane (100 mL) and aqueous sodium chloride (14 g NaCl and 80 mL water) were added to the organic layer and the reaction mixture was then stirred while bubbling air into it at 30 to 35° C. The layers were separated after the completion of the reaction and the organic layer was washed twice with aqueous sodium chloride solution (40 mL, 5%) and was then concentrated to give crude menatetrenone.

Example 4

First Step (Condensation Reaction)

Menadiol monoacetate (4) (30.5 g) was dissolved in toluene (150 mL) and methanesulfonic acid (2 mL) was added. While this solution was being stirred, all-trans-geranyllinalool (5) (27.7 g) was added dropwise over 45 minutes at 49 to 51° C., the reaction was then continued for 2 hours and 55 minutes at the same temperature. The reaction solution was washed with aqueous sodium chloride solution (40 mL, 5%) twice. The organic layer was washed three times with a solution prepared by the addition of sodium hydrosulfite (2 g) to aqueous potassium hydroxide solution (40 mL, 10%).

Second Step (Treatment with Claisen's Alkaline)

To the organic layer were added sodium hydrosulfite (4 g), potassium hydroxide (23 g), water (17 mL), and methanol (40 mL) and the mixture was stirred. The toluene layer was removed by layer separation; the aqueous layer was washed with toluene (75 mL); ethyl acetate (100 mL), n-hexane (100 mL), and water (220 mL) were added to the aqueous layer and the aqueous layer was extracted; and the organic layer was washed with aqueous sodium chloride solution (40 mL, 5%) twice, followed by layer separation.

Third Step (Oxidation Reaction)

To the organic layer were added aqueous sodium chloride (prepared from 14 g NaCl and 80 mL water) and n-hexane (200 mL) and the reaction mixture was then stirred for 3 hours while bubbling air into it at 25 to 40° C. The layers were separated after the completion of the reaction and the organic layer was washed with water (40 mL) twice and was concentrated to give crude menatetrenone.

Example 5

First Step (Condensation Reaction)

Menadiol monoacetate (4) (260.2 kg) and toluene (1300 L) were introduced into a reactor; dodecylbenzenesulfonic acid (3.5 kg) and all-trans-geranyllinalool (5) (290.5 kg) dissolved in toluene (100 L) were introduced; and hot water at 55° C. was thereafter injected through the jacket and the reaction mixture was stirred for 8 hours at an internal temperature of at least 50° C. After cooling with cold water and then reheating with 50° C. hot water, and at an internal temperature of 31.9° C., an aqueous potassium hydroxide/hydrosulfite solution (412 L) prepared from potassium hydroxide (70 kg), hydrosulfite (40 kg), and water (800 L) was added and the mixture was stirred for 20 minutes. The aqueous layer was then separated and discarded. The remaining of the aqueous potassium hydroxide/hydrosulfite solution (508 L) and water (400 L) were added to the organic layer; the mixture was stirred for 20 minutes; and the aqueous layer was then separated and discarded.

Second Step (Treatment with Claisen's Alkaline)

Hydrosulfite (30 kg) was added and the mixture was heated under a nitrogen atmosphere with 60° C. hot water. The hot water was stopped at the point at which the internal temperature had risen to 30° C.; a solution prepared from potassium hydroxide (205 kg), water (185 L), and methanol (389 L) was added; the reaction mixture was stirred for 30 minutes; and stirring was then stopped and the reaction mixture was stand for 2 hours. The organic layer was separated off; toluene (1300 L) was then added to the aqueous layer; the mixture was stirred for 5 minutes; and the organic layer was separated off and discarded. The aqueous layer was added to a stirred tank containing toluene (2000 L) and water (2200 L), the mixture was stirred for 30 minutes, glacial acetic acid (300 kg) was then added and the mixture was stirred for another 30 minutes. The aqueous layer was separated off and the organic Layer was then washed with aqueous sodium chloride solution prepared from aqueous sodium chloride solution (113 L, 10%) and water (100 L) and was additionally washed with aqueous sodium chloride solution prepared from aqueous sodium chloride solution (97 L, 10%) and water (100 L).

Third Step (Oxidation Reaction)

Water (800 L) was added to the organic layer; hot water at 60° C. was then injected through the jacket; and the reaction mixture was stirred for 15 hours under a nitrogen stream (20 Nm³/hour) at an internal temperature of 30° C. while blowing air into the reaction liquid at 20 Nm³/hour. The aqueous layer was separated off; water (300 L) was then added to the organic layer. After stirring for 10 minutes, the aqueous layer was separated off. The organic layer was washed 2 more times with water (300 L). The toluene was distilled off under reduced pressure; the residue was purified by silica gel column chromatography; and the eluting solvent was distilled off to give crude menatetrenone (219 kg).

The crude menatetrenone was dissolved with heat in 20% acetone-ethanol (2367 L). After then cooling the solution, seed crystals (25 g) were introduced at 11° C., cooling was continued down to −26.3° C. The precipitated crystals were collected by filtration and washed with 20% acetone-ethanol (704 L). The solvent was then eliminated by blowing nitrogen gas over the precipitate at 3.8 Nm³/hour for 20 hours while heating with 60° C. hot water, giving menatetrenone (1) (121.71 kg).

We claim:

1. A method for producing a compound represented by the following formula (1):

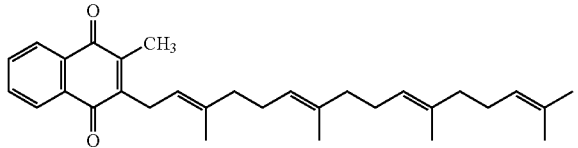

(1)

comprising the step of;
treating with an oxygen source a reaction solution consisting essentially of a solution of a compound represented by the following formula (2) dissolved in a solvent:

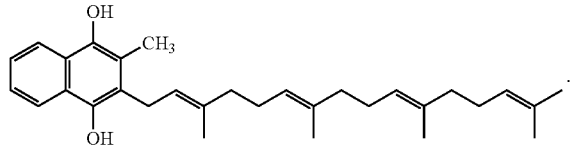

(2)

2. A method for producing a compound represented by the following formula (1):

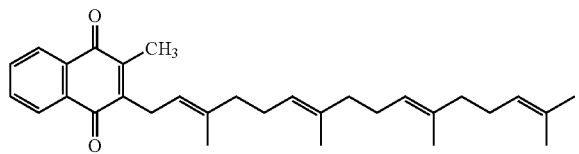

comprising the step of;
treating with an oxygen source a reaction solution consisting essentially of:

i) a solution of a compound represented by the following formula (2)

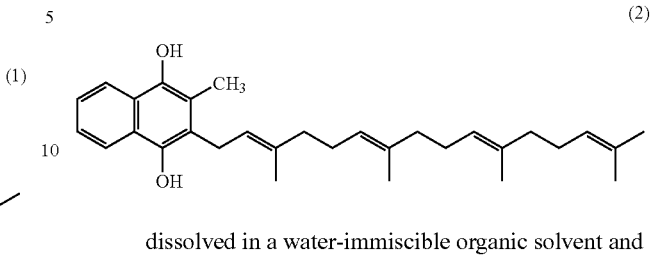

dissolved in a water-immiscible organic solvent and
ii) water or aqueous sodium chloride solution.

3. The method according to claim 1 or 2, wherein the oxygen source is air.

* * * * *